(12) United States Patent
McGrath (10) Patent No.: US 8,460,176 B2
(45) Date of Patent: Jun. 11, 2013

(54) ADAPTOR FOR AN ENDOSCOPE (75) Inventor: Darach McGrath, Nenagh (IE)

(73) Assignee: Cook Medical Technologies LLC, Bloomington, IN (US)

( * ) Notice: Subject to any disclaimer, the term of this patent is extended or adjusted under 35 U.S.C. 154(b) by 397 days.

(21) Appl. No.: 12/767,243

(22) Filed: Apr. 26, 2010

(65) Prior Publication Data

US 2010/0280311 A1 Nov. 4, 2010

Related U.S. Application Data

(60) Provisional application No. 61/173,780, filed on Apr. 29, 2009.

(51) Int. Cl.
*A61B 1/00* (2006.01)
(52) U.S. Cl.
USPC .......................................... 600/104
(58) Field of Classification Search
USPC .................... 600/104, 106, 153–159
See application file for complete search history.

(56) References Cited

U.S. PATENT DOCUMENTS

| | | | |
|---|---|---|---|
| 5,863,286 A | 1/1999 | Yabe | |
| 6,110,104 A | 8/2000 | Suzuki et al. | |
| 6,910,581 B2 * | 6/2005 | McMichael et al. | 206/571 |
| 7,234,597 B2 * | 6/2007 | Rowe et al. | 206/438 |
| 7,815,045 B2 * | 10/2010 | Delaney et al. | 206/364 |
| 8,042,689 B2 * | 10/2011 | Frojd et al. | 206/464 |
| 2003/0028096 A1 | 2/2003 | Niwa et al. | |
| 2004/0230268 A1 | 11/2004 | Huff et al. | |
| 2005/0033319 A1 | 2/2005 | Gambale | |
| 2005/0267417 A1 | 12/2005 | Secrest | |
| 2007/0270640 A1 | 11/2007 | Dimitriou et al. | |

FOREIGN PATENT DOCUMENTS

| | | |
|---|---|---|
| EP | 0 664 991 A2 | 8/1995 |
| JP | 2001 218733 A | 8/2001 |
| JP | 2002/078668 A | 3/2002 |
| WO | WO 2006/094044 A1 | 9/2006 |
| WO | WO 2009/029106 A1 | 3/2009 |
| WO | WO 2009/100106 A1 | 8/2009 |

OTHER PUBLICATIONS

International Search Report mailed Aug. 2, 2010 for International Application No. PCT/US2010/032398.
Written Opinion mailed Aug. 2, 2010 for International Application No. PCT/US2010/032398.
Patent Examination Report No. 1 dated Dec. 21, 2012 for Australian Application No. 2010241834.

* cited by examiner

*Primary Examiner* — W B Perkey
(74) *Attorney, Agent, or Firm* — Brinks Hofer Gilson & Lione (57) ABSTRACT

An adaptor and a kit including an adaptor are provided. The adaptor is configured to connect an elongate medical device to an endoscope. The adaptor includes a first portion having a distal end sized and shaped to connect to an endoscope. The first portion includes a first opening defined therethrough. The adaptor further includes a second portion connectable to the first portion and including a second opening defined through the second portion and operably connectable to the first lumen. The second portion includes a connector at a proximal end portion sized and shaped to receive at least a portion of the elongate medical device so that a shaft of the elongate medical device is extendable distally through the first opening and the second opening and into the endoscope when the elongate medical device is connected to the adaptor.

20 Claims, 12 Drawing Sheets

ADAPTOR FOR AN ENDOSCOPE

CROSS-REFERENCE TO RELATED APPLICATIONS

This application claims the benefit of U.S. Provisional Application No. 61/173,780, filed Apr. 29, 2009, which is incorporated herein by reference in its entirety.

TECHNICAL FIELD

This invention generally relates to an adaptor for receiving elongate medical devices that are insertable into an endoscope, and in particular to an adaptor for connecting to an accessory channel port of an endoscope.

BACKGROUND

Endoscopic devices and procedures may be used to diagnose, monitor and treat various conditions by close examination of the internal organs. By way of background, a conventional endoscope generally is an instrument having a device for visualizing the interior of an internal region of a body and a lumen for inserting one or more treatment devices therethrough. A wide range of applications have been developed for the general field of endoscopes including by way of example the following: arthroscope, angioscope, bronchoscope, choledochoscope, colonoscope, cytoscope, duodenoscope, enteroscope, esophagogastro-duodenoscope (gastroscope), laparoscope, laryngoscope, nasopharyngoneproscope, sigmoidoscope, thoracoscope, and utererscope (individually and collectively, "endoscope").

In some endoscopic devices, visualization of the internal regions may be obtained using a video camera. The video camera provides a viewing field to observe the surgical instrumentation or procedure within the viewing field. Medical ultrasound has also been used to monitor a surgical procedure within a viewing field. Endoscopic ultrasound (EUS) utilizes high frequency sound waves to create an image of living tissue or an echogenic surface. Ultrasound waves are emitted from transducers located at the distal end of an endoscope. Surgical instruments having an echogenic surface reflect the ultrasound waves and enable an endoscopist to monitor the location of the device within the patient.

In some procedures, medical devices are inserted through the endoscope to access the internal organs. For example, an elongate device, such as a needle, may be inserted through an accessory channel of the endoscope for diagnostic and therapeutic procedures.

Endoscopes manufactured by different companies may have different types of connectors at the accessory channel port for connecting with elongate medical devices. The different type of connector at the accessory channel port requires that each elongate medical device include the appropriate connector for each different type of endoscope. The requirement for different connectors on a variety of different types of elongate medical devices greatly increases the need for increased inventory of the medical devices, depending on the type of endoscope that will be used during a medical procedure. The increased inventory also increases the costs associated with these medical procedures.

It is desirable to have an adaptor that is universally connectable to the accessory channel port of any type of endoscope, and which includes a portion that is sized and shaped to receive an elongate medical device chosen by the endoscopist.

SUMMARY OF THE INVENTION

Accordingly, it is an object of the present invention to provide an adaptor for an endoscope having features that resolve or improve on one or more of the above-described drawbacks.

The foregoing object is obtained in one aspect of the present invention by providing an adaptor configured to connect an elongate medical device to an endoscope, the adaptor and the endoscope having non-compatible connectors. The adaptor includes a first portion having a distal end sized and shaped to connect to an endoscope. The first portion includes a first opening defined therethrough. The adaptor further includes a second portion connectable to the first portion and including a second opening defined through the second portion and operably connectable to the first opening. The second portion includes a connector at a proximal end portion sized and shaped to receive at least a portion of the elongate medical device so that a shaft of the elongate medical device is extendable distally through the first opening and the second opening and into the endoscope when the elongate medical device is connected to the adaptor.

In another aspect, a kit is provided. The kit includes at least one adaptor provided in a packaging. The kit may include a plurality of adaptors. The kit may include an elongate medical device.

In another aspect, an adaptor is provided for connecting an elongate medical device to an endoscope, the elongate medical device and the endoscope having non-compatible connectors. The adaptor includes a first portion having a body shaped to connect to an endoscope, the first portion having a first opening defined therethrough and the first portion laterally engagable with the connector on the endoscope such that a surface of the first portion abuts a portion of a flange of the connector. The adaptor includes a second portion connectable to the first portion and including a second opening defined through the second portion and operably connectable to the first opening. The second portion has an adaptor connector at a proximal end portion, the adaptor connector being sized and shaped to receive at least a portion of the elongate medical device so that a shaft of the elongate medical device is extendable distally through the first opening and the second opening and into the endoscope when the elongate medical device is connected to the adaptor.

Advantages of the present invention will become more apparent to those skilled in the art from the following description of the preferred embodiments of the invention which have been shown and described by way of illustration. As will be realized, the invention is capable of other and different embodiments, and its details are capable of modification in various respects. Accordingly, the drawings and description are to be regarded as illustrative in nature and not as restrictive.

DETAILED DESCRIPTION OF THE EMBODIMENTS

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician operating an endoscope and an elongate medical device for insertion into a patient. Hence the term distal means the portion of the device that is farthest from the physician and the term proximal means the portion of the device that is nearest to the physician.

Figure 1:
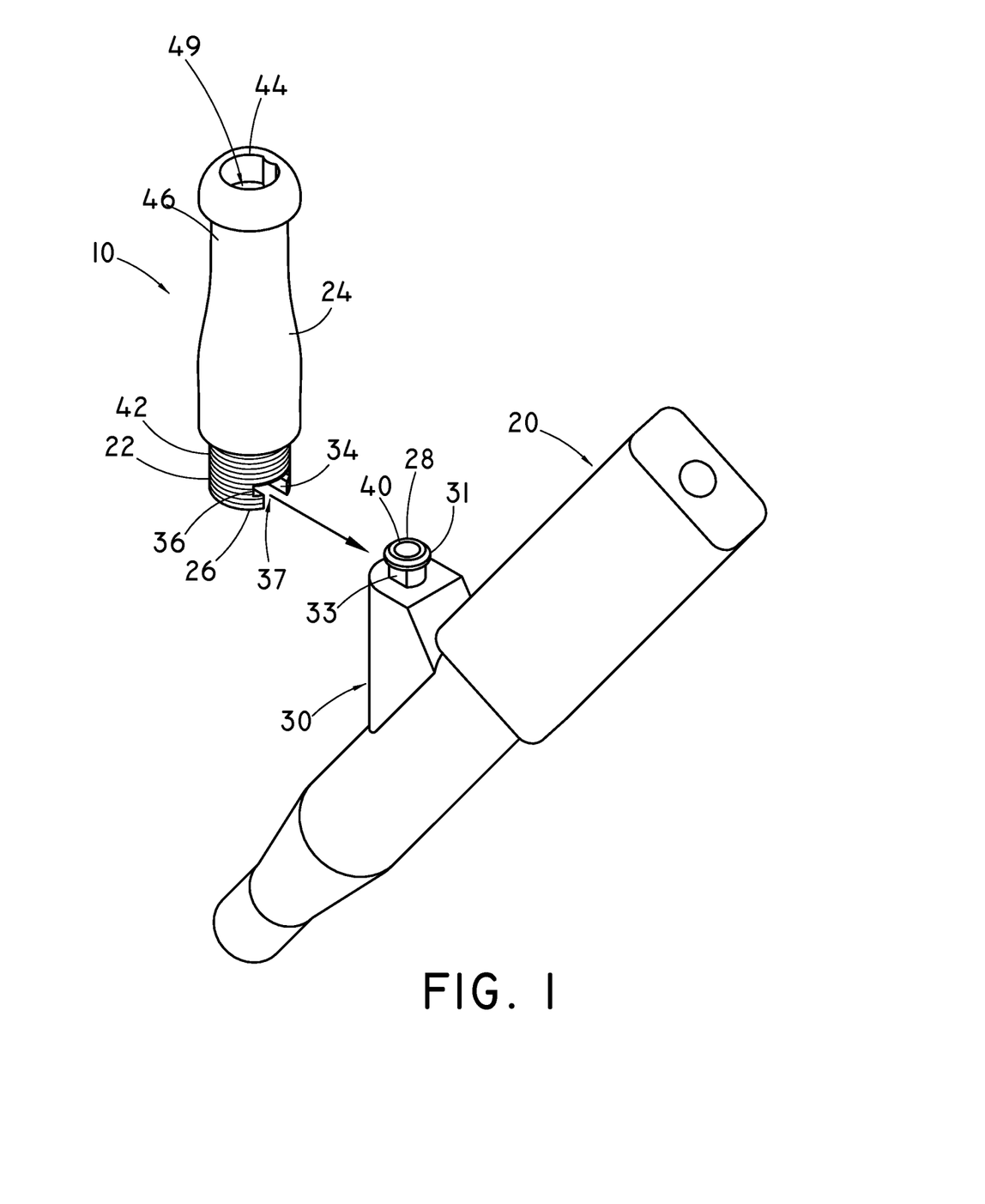
FIG. 1 is a partial side perspective view of an adaptor according to the present invention.

FIG. 1 illustrates an adaptor 10 in accordance with embodiments of the present invention. The adaptor 10 is configured for removable connection to an endoscope 20. The adaptor 10 includes a first portion 22 and a second portion 24. The first portion 22 and the second portion 24 may be independently movable in relation to each other and may further be releasably connectable to each other.

As shown in FIG. 1, the first portion 22 of the adaptor 10 includes a distal end portion 26 that may be connected to a connector 28 on an accessory channel 30 of the endoscope 20. The distal end portion 26 is sized and shaped to complimentarily engage the connector 28. The distal end portion 26 may be provided in different sizes and shapes depending on the type of endoscope connector that is provided with the endoscope. By way of non-limiting example, the connector 28 may include a flange 31 and two flat sides 33 as shown in FIG. 1. The distal end portion 26 of the first portion 22 includes two internal complimentarily corresponding flat sides 34 that are configured to mate with the flat sides 33 of the connector 28. The distal end portion 26 further includes a slot 36 sized and shaped to engage the lip of the flange 31 on connector 28 and an opening 37 in the wall of the distal end portion 26 so that the slot 36 can laterally slide over the connector 28. The slot 36 of the first portion 22 secures the adaptor 10 to the connector 28 of the endoscope 20 so that the adaptor 10 is longitudinally fixed relative to the connector 28. A lumen 48 extends through the first portion 22 and is operably connected to the accessory channel 30 of the endoscope 20 as shown in FIG. 4.

Figures 2, 3:
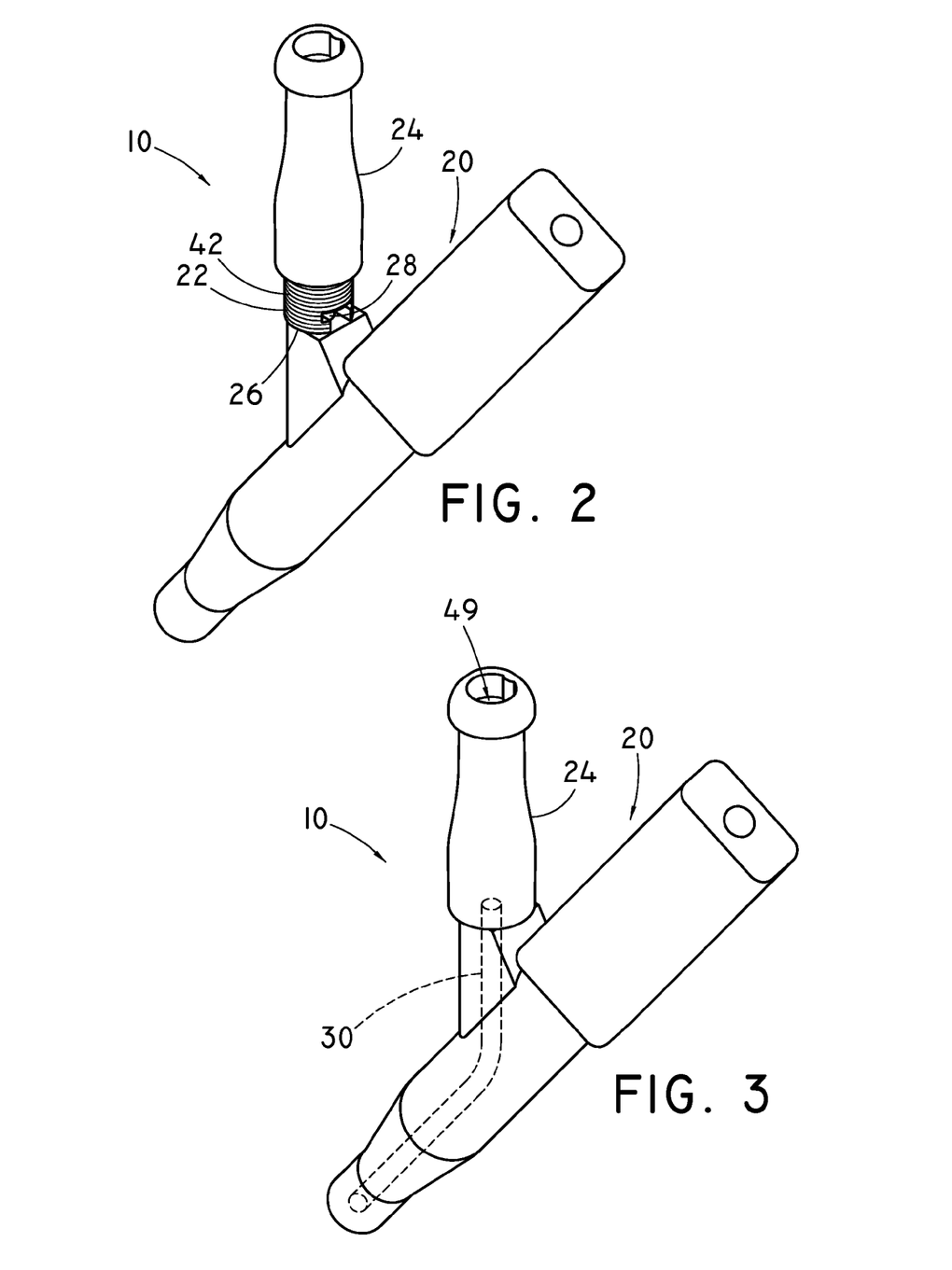
FIG. 2 is partial a side perspective view of the adaptor shown in FIG. 1 with a first portion of the adaptor partially connected to an endoscope.
FIG. 3 is a partial side perspective view of the adaptor shown in FIG. 1 with the adaptor connected to the endoscope.

FIG. 2 illustrates the adaptor 10 with the distal end portion 26 connected to the connector 28 of the endoscope 20. The second portion 24 of the adaptor 10 may be moved relative to the first portion 22 of the adaptor 10 to further secure the adaptor 10 to the endoscope 20. The second portion 24 may be secured relative to the first portion 22 by any mechanism known to one skilled in the art, for example, by threads or snap fit connection. As shown in FIG. 2, the first portion 22 includes external threads 42 that may be threaded together with internal threads 68 on the second portion 24 (shown in FIG. 4) to thread the second portion 24 over the first portion 22 to axially secure the adaptor 10 to the connector 28 of the endoscope 20. A lumen 49 extends through the second portion 24 and operably connects to the lumen 48 of the first portion 22.

FIG. 3 illustrates the second portion 24 of the adaptor 10 secured over the first portion 22. The second portion 24 engages the first portion 22 so that the opening 37 is closed by the second portion 24 and the slot 36 and the flat sides 33 are pressed against the connector 28 so that fluid and air does not leak from the connection between the first portion 22 and the connector 28.

Figure 4:
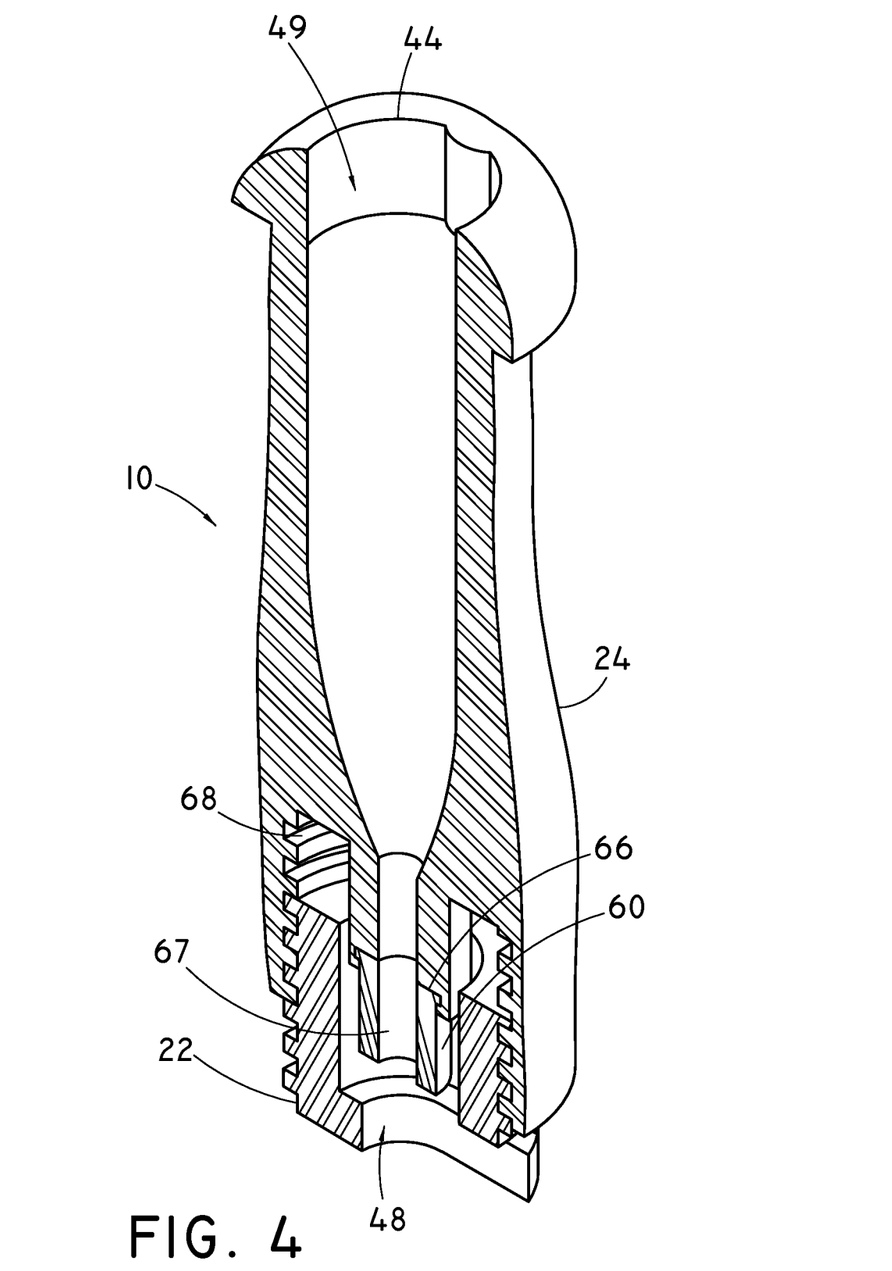
FIG. 4 is a cross-sectional view of an adaptor according to the present invention.

A sectional view of the adaptor 10 before the adaptor 10 is secured to the endoscope is shown in FIG. 4. In addition to the first section 22 and the second section 24, the adaptor 10 may further include a seal 60 that may be positioned within the adaptor 10 and tightens over the connector 28 in combination with the first portion 22. The seal 60 facilitates sealing of the adaptor 10 against the connector 28 so that fluid does not leak out and suction can be maintained when desired. A channel 67 is provided through the seal 60 so that lumen 49 in the adaptor 10 may be operably connected to the accessory channel 30 of the endoscope 20. The seal 60 may be sized and shaped to abut against a distal cavity wall 66 in the second portion 24 and into the first portion 22. As the internal threads 68 of the second portion 24 tighten down over the external threads 42 of the first portion 22, the slot 36 of the first portion 22 tightens against the connector 28 and the seal 60 slides into the first portion 22 and tightens against the top of the connector 28.

Additional configurations of the first portion 22 and the second portion 24 are possible for connecting with the connector 28 of the endoscope 20, as will be understood by one skilled in the art. The first portion 22 may be modified to complimentarily engage a different type of connector 28. For example, if the connector 28 is a typical luer-type connector with a round base under a protruding flange instead of the base having the flattened sides shown in FIG. 1, the first portion 22 of the adaptor 10 may include the slot 36 with a rounded internal face instead of the flattened sides 33.

As shown in FIG. 3, the lumen 49 extends through the adaptor 10 and is operably connected with an opening 40 (shown in FIG. 1) within the connector 28 so that the lumen 49 of adaptor 10 connects to the accessory channel 30 of the endoscope 20. The adaptor 10 is longitudinally and axially secured to the endoscope 20 and is ready to receive an elongate medical device 50 therethrough. The elongate medical device 50 may be any kind of device that is normally inserted through the accessory channel of an endoscope. The second portion 24 of the adaptor 10 includes an opening 44 in a proximal portion 46 that is sized and shaped to receive the elongate medical device 50. An exemplary type of elongate medical device that may be used with the adaptor of the present invention is an echogenic needle with a multipart handle assembly. An exemplary handle suitable for use with the adaptor of the present invention is described U.S. Pat. No. 6,976,955. An exemplary needle is the Echotip® Ultra Endoscopic Ultrasound Needle (Cook Medical, Bloomington, Ind.).

Figure 5:
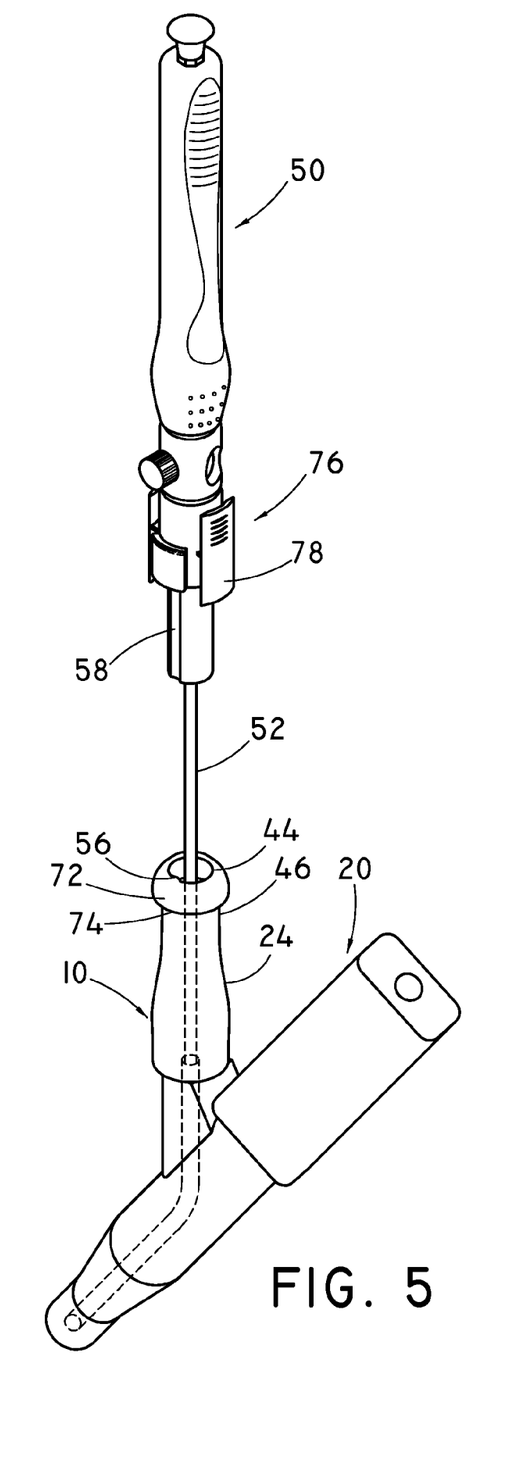
FIG. 5 is a partial side perspective view of the adaptor shown in FIG. 3 and an elongate medical device.

As shown in FIG. 5, the elongate medical device 50 is insertable into the endoscope 20 through an adaptor 10 that has been secured to the connector 28. By way of non-limiting example, an exemplary elongate medical device 50 is shown with a shaft portion 52 extending into the opening 44 at the proximal end portion 46 of the adaptor 10. The proximal end portion 46 may include an orienting key 56 that protrudes into the opening 44 and is configured to mate with a keyway 58 on a portion of the elongate medical device 50 to orient the elongate medical device 50 in the accessory channel 30 of the endoscope 20. In some embodiments, the adaptor 10 may be provided with the keyway and the elongate medical device provided with the key.

The adaptor 10 may further include a securing portion 72 at the proximal end portion 46 for securing at least a segment of the elongate medical device 50 to the adaptor 10. Additional segments of the elongate medical device 50 may be longitudinally moveable in relation to the adaptor 10 and the endoscope 20 so the a distal end of the elongate medical device 50 may be extended out of the distal end of the endoscope to perform a procedure (not shown). As shown in FIG. 5, distal end portion 46 of the adaptor 10 may include a flange 74 extending radially outwardly from the adaptor 10 as a type of securing portion 72. The elongate medical device 50 may include a corresponding securing portion 76, such as one or more clips 78 to secure the elongate medical device 50 to the adaptor 10.

Figure 6:
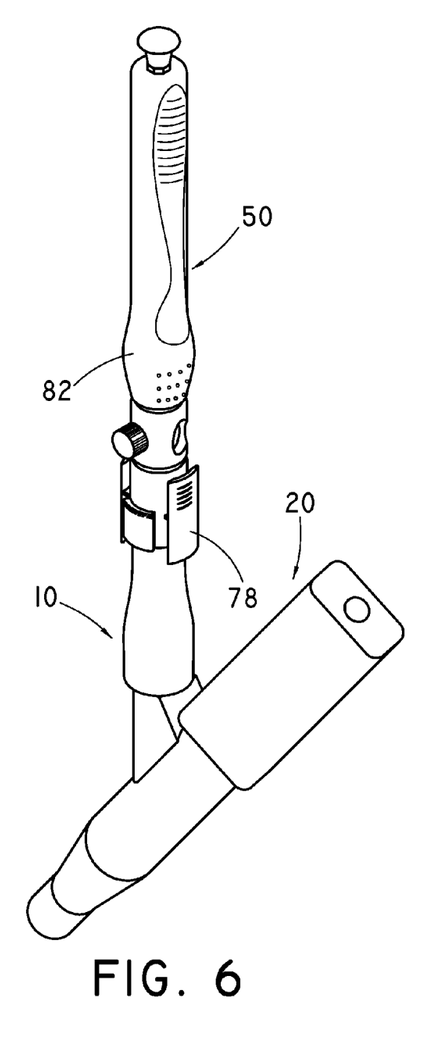
FIG. 6 is a partial side perspective view of the adaptor shown in FIG. 5 with the elongate medical device connected thereto.
Figure 7:
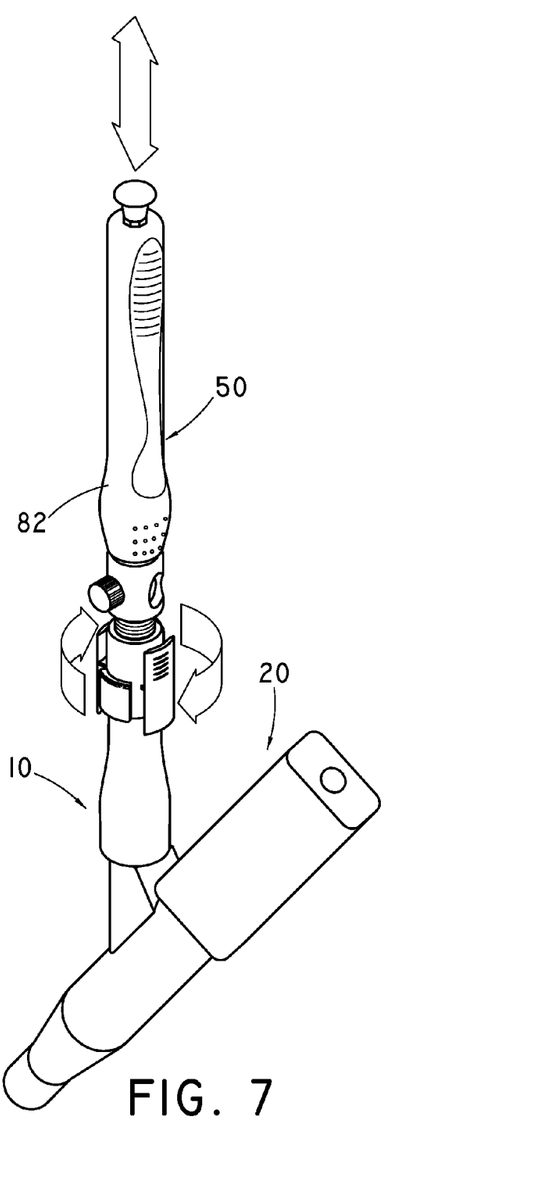
FIG. 7 is a partial side perspective view of the adaptor and elongate medical device shown in FIG. 6 and illustrating the motion of the medical device.

FIGS. 6 and 7 illustrate the elongate medical device 50 secured to an adaptor 10 that has been secured to the endoscope 20. The shaft 52 extends through the lumen 38 of the adaptor 10 and into the accessory channel 30 of the endoscope 20. The elongate medical device 50 includes a handle 82 that may be manipulated to move the shaft 52 longitudinally through the working channel 30. The handle 82, or portions thereof, may be rotated in relation to the adaptor 10, with the elongate medical device 50 still secured to the adaptor 10 with the clips 78 of the medical device 50 secured to the flange 74 of the adaptor 10. Rotation of the handle 82 allows for the longitudinal movement of the shaft 52 as illustrated in FIG. 7. In addition, when an orienting key 56 and keyway 58 are included, the shaft 52 of the elongate medical device 50 retains the axial orientation within the adaptor 10 and in relation to the endoscope 20 while the handle 82 is rotatable and the elongate device 50 is longitudinally moveable.

Figures 8, 9:
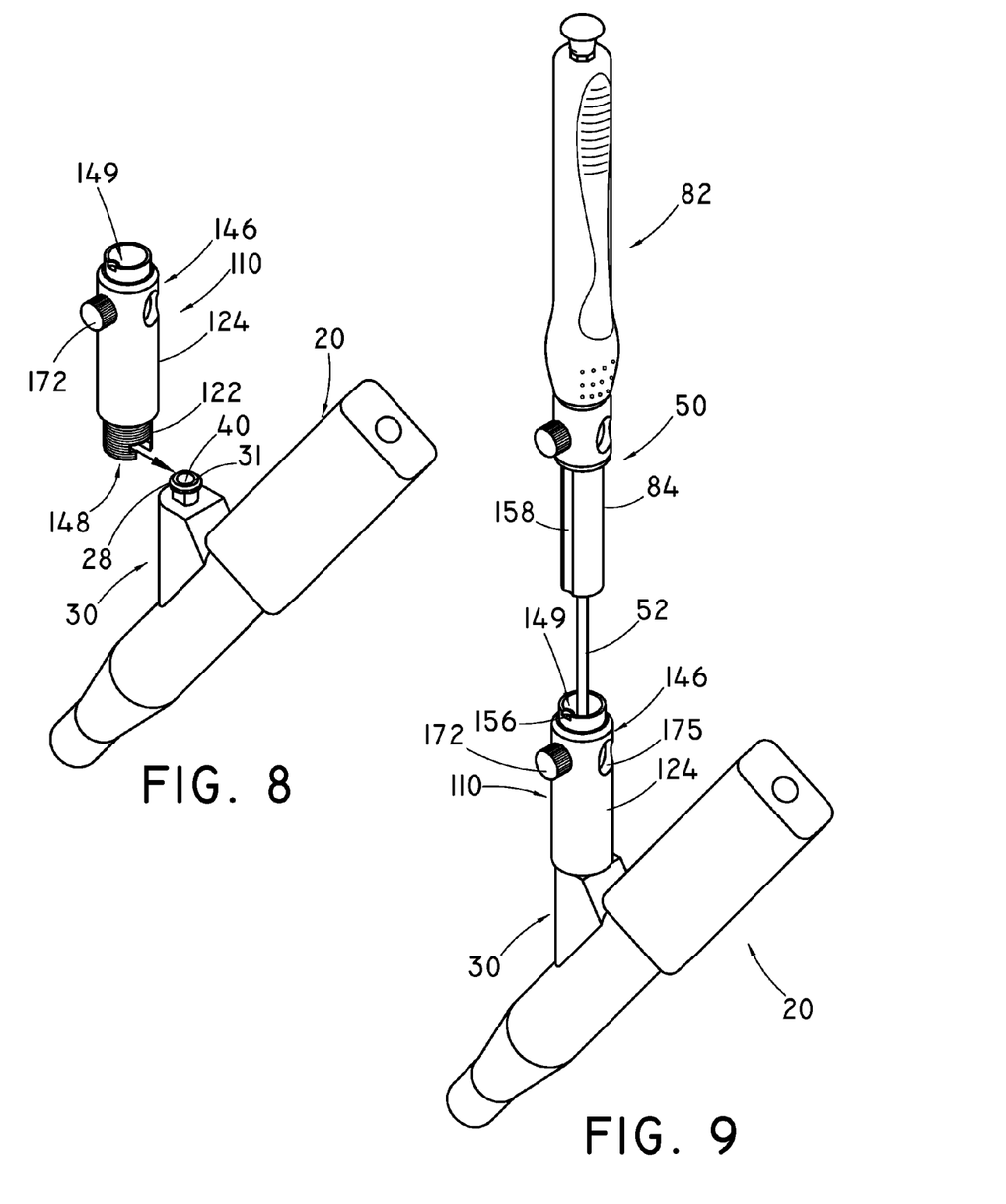
FIG. 8 is a partial side perspective view of an alternative adaptor according to the present invention.
FIG. 9 is a partial side perspective view of the adaptor shown in FIG. 8 and an elongate medical device.

An alternative embodiment of the adaptor of the present invention is shown in FIGS. 8 and 9. FIG. 8 illustrates an adaptor 110 having a first portion 122 and a second portion 124. Similar to the adaptor 10 described above, the first portion 122 is sized and shaped to complimentarily engage the connector 28 of the endoscope 20. The first portion 122 is sized and shaped to complimentarily engage the specific connector shape depending on the manufacturer of the endoscope. The first portion 122 is secured to the connector 28 in a manner similar to the adaptor 10 described above.

The adaptor 110 includes the second portion 124 that is configured to further secure the first portion 122 to the connector 28 of the endoscope 20 similar to the adaptor 10 described above. The proximal end portion 146 illustrates an alternative securing portion 172 on the adaptor 110 that is designed to mate with the handle 82 of the elongate medical device 50 (shown in FIG. 9) to secure a portion 84 of the handle 82 to the adaptor 110. As described below, a key or keyway may also be included to rotationally orient the medical device. The securing portion 172 may be a rotatable thumb screw that presses against the handle portion 84 to secure the elongate medical device 50 in the adaptor 10. The adaptor 110 may also include a side wall opening 175 for viewing a portion of the elongate medical device 50 such as a numerical marking to indicate how far into the adaptor 110 the handle portion 84 extends and thus also indicates a position of the elongate medical device 50 in relation to the endoscope 20.

Similar to the second portion 24 of the adaptor 10, the second portion 124 may include one of a key 156 or a keyway 158 to rotationally orient the elongate medical device 50 in relation to the endoscope 20. Similar to the adaptor 10 described above, the first portion 122 and the second portion 124 include lumens 148, 149 extending therethrough and operably connecting to the accessory channel 30 of the endoscope 20 when the adaptor 110 is secured to the endoscope 20. As shown in FIG. 9, the shaft 52 of the medical device 50 extends through the lumen 149 and into the accessory channel 30 of the endoscope 20. The securing portion 172 may be tightened against the handle portion 84 once the handle portion 84 is positioned in the distal end portion 146 of the adaptor 110 and the key 156 and the keyway 158 are mated to orient a portion of the elongate medical device 50. When the securing portion 172 is tightened against the handle portion 84, the shaft 52 of the elongate medical device 50 retains the axial orientation within the adaptor 110 and in relation to the endoscope 20 while a portion of the handle 82 is rotatable and the shaft 52 of the elongate device 50 are longitudinally moveable relative to the endoscope 20.

Figure 10:
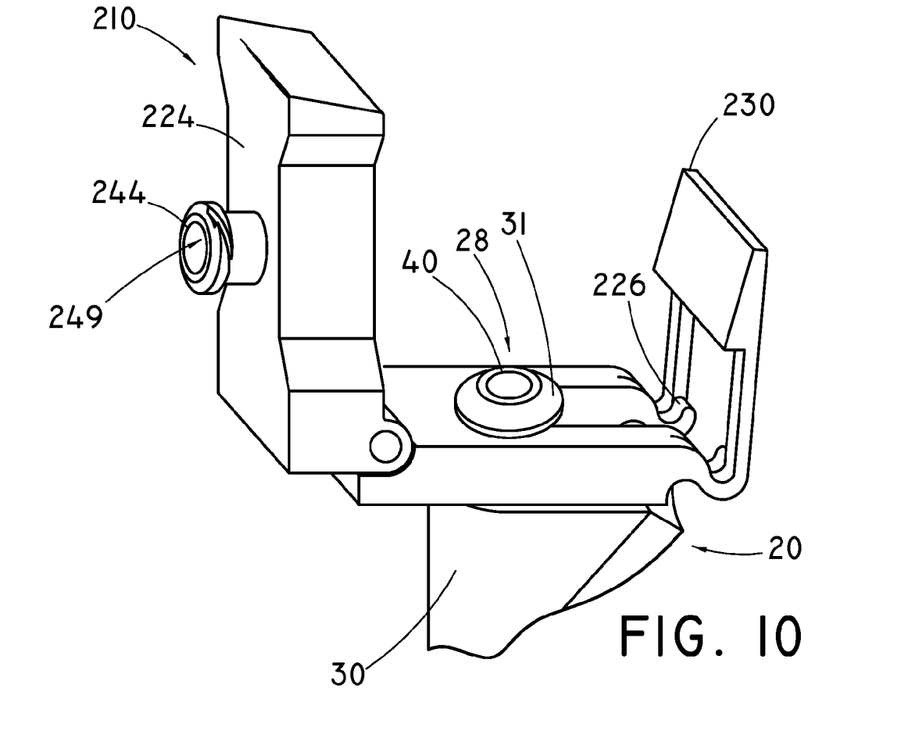
FIG. 10 is a partial side perspective view of an alternative adaptor according to the present invention in an open position.
Figure 11:
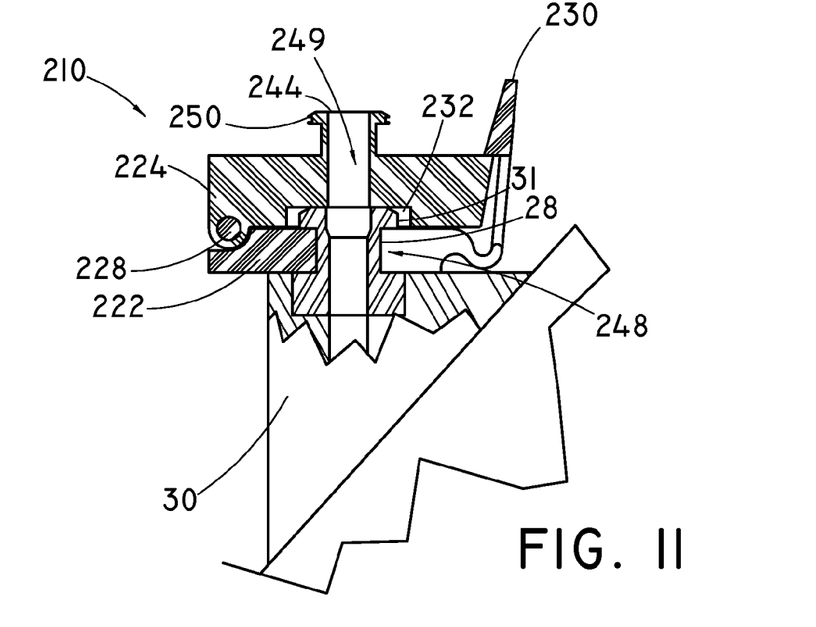
FIG. 11 is a partial side perspective view of the adaptor shown in FIG. 10 in the closed position.

FIGS. 10 and 11 illustrate an alternative embodiment of the adaptor of the present invention. An adaptor 210 is shown in FIG. 10 having a first portion 222 and a second portion 224. The first portion 222 is configured to complimentarily engage the connector 28 of the endoscope 20. The first portion 222 includes a pair of flexible legs 226 including an opening 248 therebetween. The legs 226 are flexible enough to slide underneath a flange 31 on the connector 28 and around the connector 28 so that the adaptor 210 can be secured to the connector 28 of the endoscope 20. The second portion 224 of the adaptor 210 may be connected to the first portion 222 by a hinge 228 as shown in FIG. 10. Alternatively, the second portion 224 may be provided separately from the first portion 222. The adaptor 210 may be provided with the hinge 228 in an open position so that the first connector 222 can be slid over the connector 28 and then the second portion 224 may be secured over the connector 28 and to the first portion 222 by a closure 230 so that the flange 31 is secured between the first portion 222 and the second portion 224. In some embodiments, the closure 230 is formed integrally with the first portion 222 and snaps over the second portion 224 to secure the adaptor 210 to the connector 28. Alternatively, the closure 230 may be provided as a separate piece that secures the first portion 222 together with the second portion 224 and onto the connector 28.

As shown in FIG. 11, the second portion 224 includes a recess 232 that is sized and shaped to receive the flange 31 of the connector 28 and form a seal against the connector 28. Similar to the embodiment described above, a separate sealing member may be provided (not shown). The second portion 224 includes an opening 244 to a lumen 249 extending through the second portion 224 and operably connecting to the opening 40 of the accessory channel 30 of the endoscope 20. A luer-type connector 250 may be provided at the opening 244 for simple connection of an elongate medical device to the adaptor 210. Any type of connector 250 that connects with the desired elongate medical device may be provided on the second portion 224 of the adaptor 210. The elongate medical device can be connected to the connector 250 of the adaptor 20 so that the shaft of the elongate medical device extends through the openings 244 and 40 and into the accessory channel 30.

Figure 12:
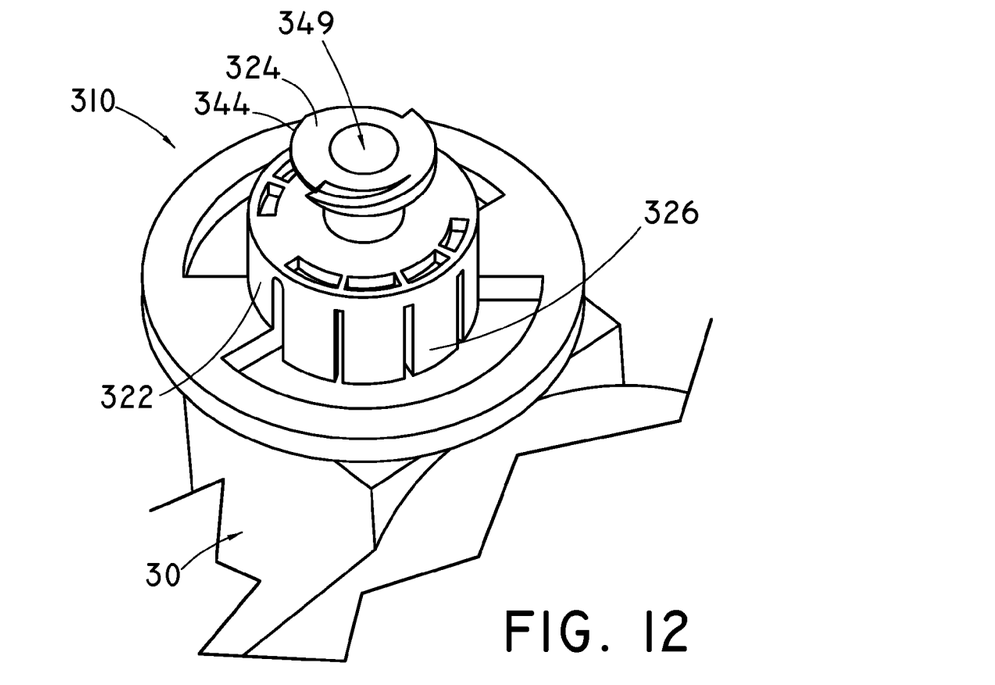
FIG. 12 is a partial side perspective view of an alternative adaptor according to the present invention.
Figure 13:
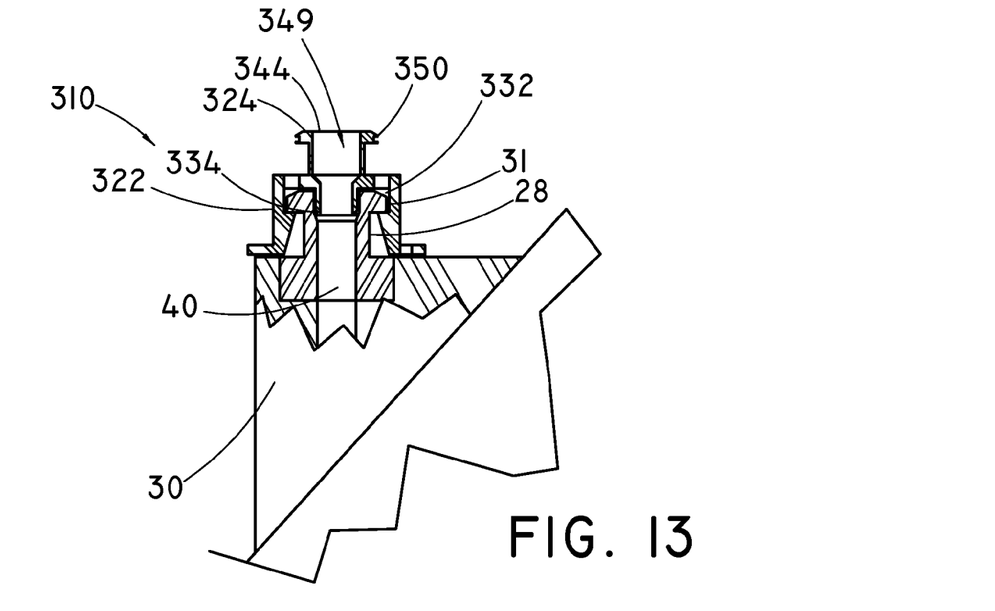
FIG. 13 is a side sectional view of the adaptor shown in FIG. 12.

FIGS. 12 and 13 illustrate an alternative embodiment of the adaptor of the present invention. An adaptor 310 is shown in FIG. 12 having a first portion 322 and a second portion 324. The first portion 322 is configured to complimentarily engage the flange 31 the connector 28 of the endoscope 20. The first portion 322 includes flexible legs 326 that are flexible enough to expand outwardly to expand over the connector 28 and then to return to the original configuration and snap in under the flange 31 of the connector 28. As shown in FIG. 13, the adaptor 310 is secured against the connector 28 and secured to the endoscope 20.

As shown in FIG. 13, the adaptor 310 includes a recess 332 that is sized and shaped to receive the flange 31 of the connector 28 and includes a seal 334 that seals against the connector 28. The seal 334 may be provided as an integral part of the adaptor 310. Alternatively, the seal 334 may be provided as a separate piece. The second portion 324 includes an opening 344 of a lumen 349 extending through the second portion 324 and the seal 334 and operably connecting to the opening 40 of the accessory channel 30 of the endoscope 20. The second portion 324 may be formed integrally with the first portion 322 to provide a unitary adaptor 310. A luer-type connector 350 may be provided at the opening 344 for simple connection of an elongate medical device to the adaptor 310. Any type of connector 350 that easily connects with the desired elongate medical device may be provided on the second portion 324 of the adaptor 310. The elongate medical device can be connected to the connector 250 of the adaptor 20 so that the shaft of the elongate medical device extends through the opening 344, the seal 334 and opening 40 and into the accessory channel 30.

Figure 14:
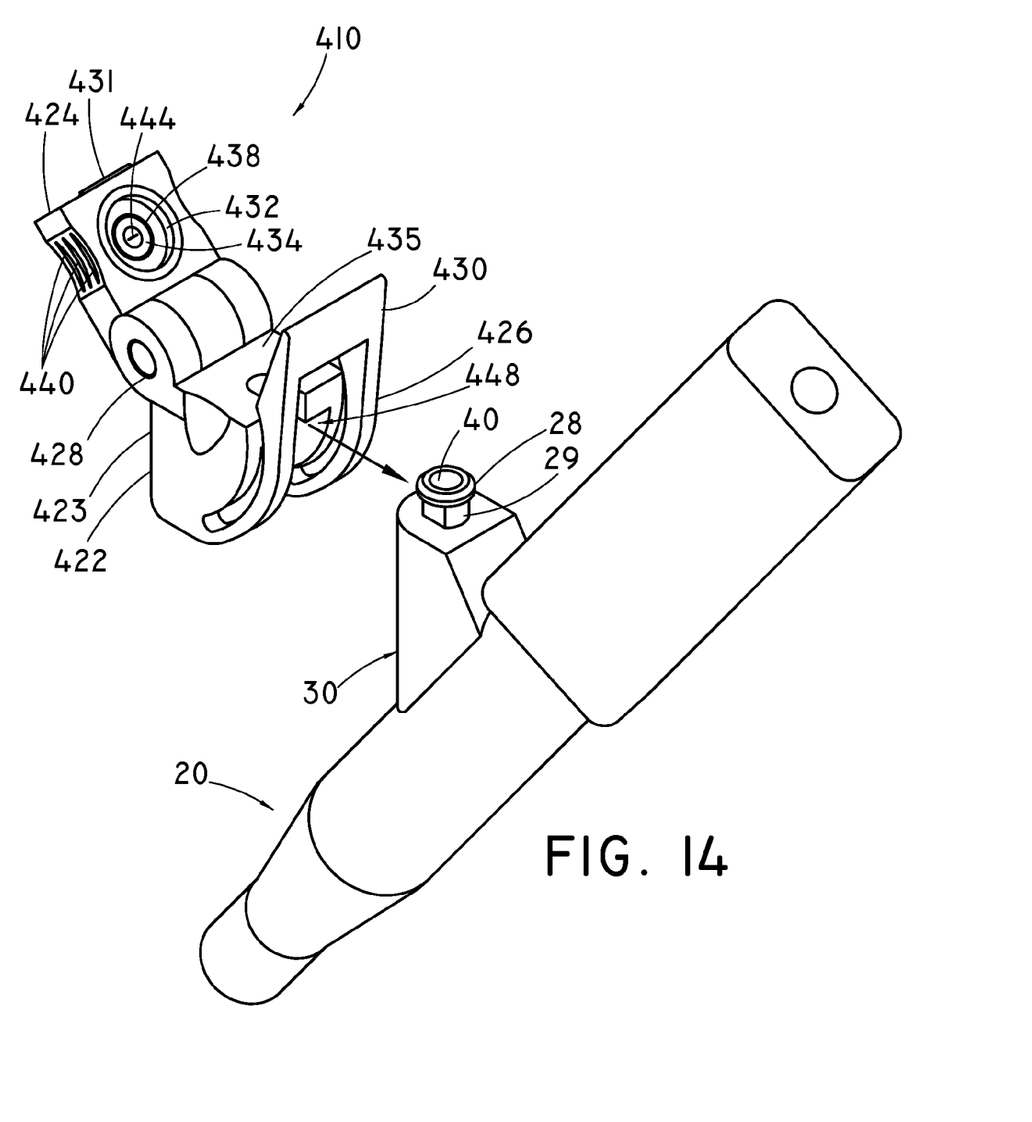
FIG. 14 is a perspective view of an alternative adaptor according to the present invention.
Figure 15:
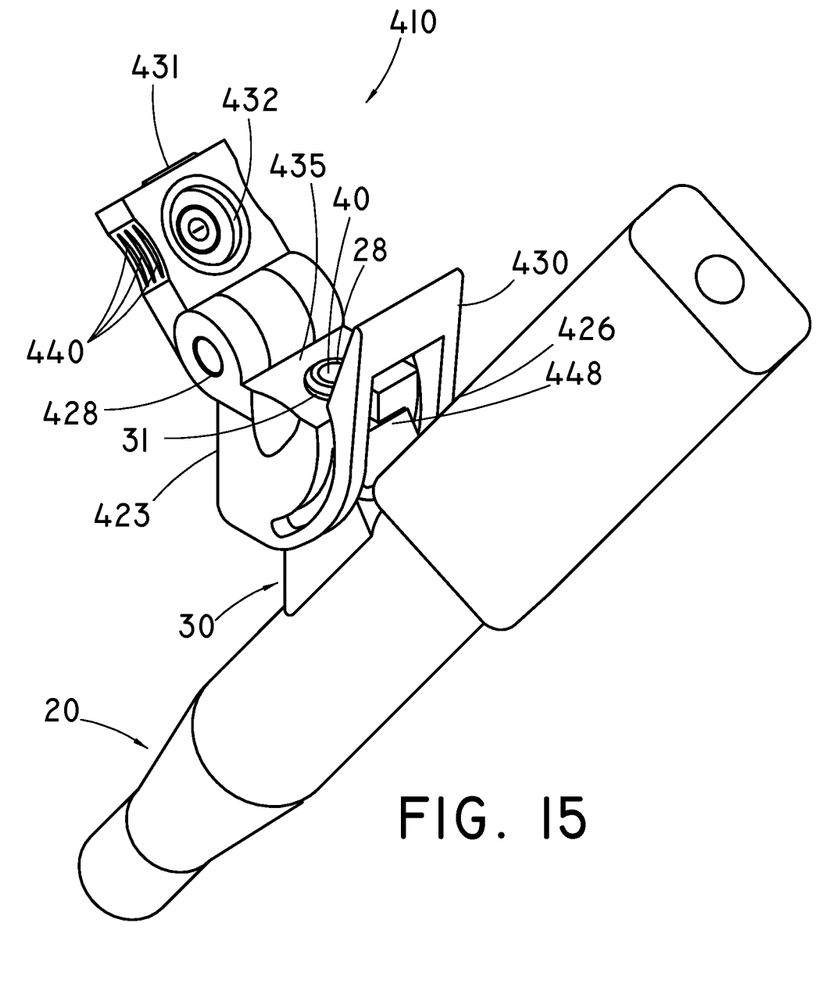
FIG. 15 is a perspective view of the adaptor shown in FIG. 14 closely fit to an accessory channel.
Figure 16:
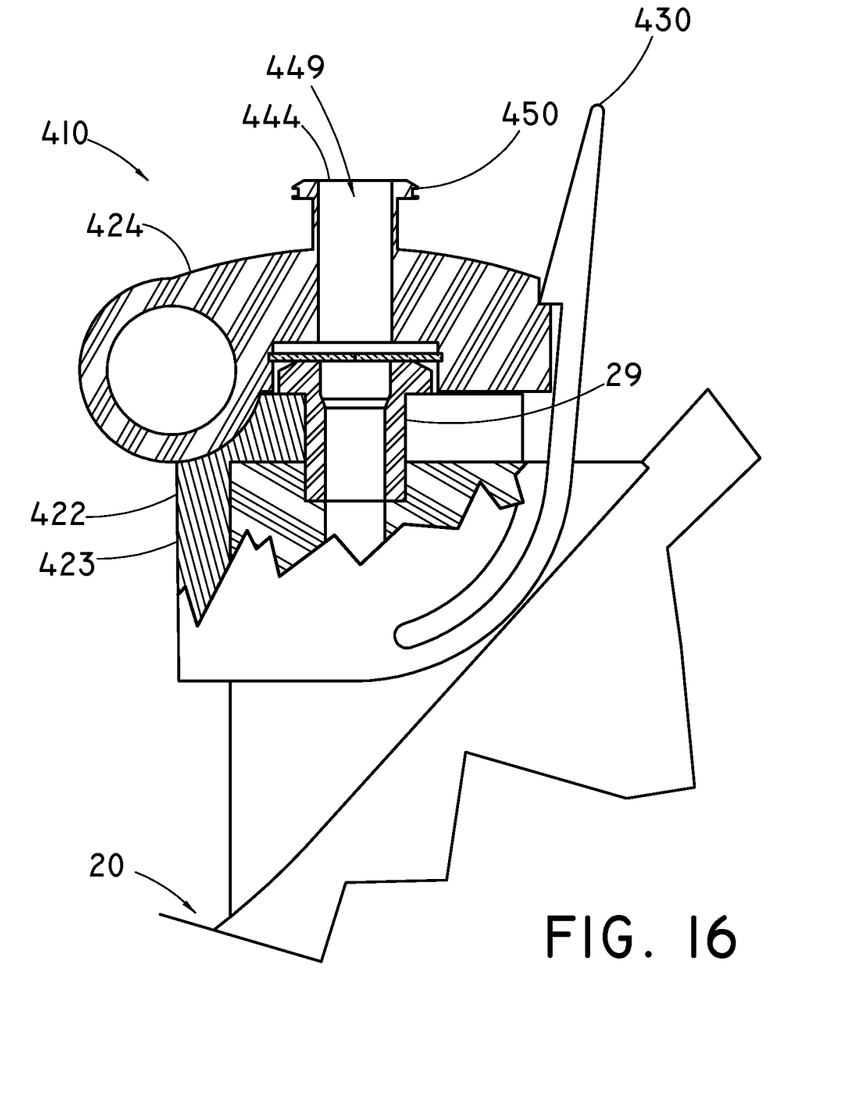
FIG. 16 is a perspective view of the adaptor shown in FIG. 15 with the adaptor closed and connected to the accessory channel.

FIGS. 14, 15 and 16 illustrate an alternative embodiment of the adaptor of the present invention. An adaptor 410 is shown in FIG. 14 having a first portion 422 and a second portion 424. The first portion 422 is configured to complimentarily engage the endoscope 20 and fit around a stem portion 29 and beneath a flange 31 of the connector 28 of the accessory channel 30. The first portion 422 includes an opening 448 extending through the first portion 422 and defined by a body portion 423 that is sized and shaped to fit closely with the accessory channel 30 of the endoscope 20. The first portion 422 is configured to laterally slide over the accessory channel portion of the endoscope 20 so that a surface 435 of the first portion 422 slides beneath the flange 31 of the connector 28. In some endoscopes 20, as described above, the connector 28 may be provided with flat side portions on the stem portion 29. Depending on the endoscope 20, the flat side portions may be in different orientations. The opening 448 in the first portion 422 of the adaptor 410 allows the body portion 423 of the first portion 422 to hug the accessory channel 30 and fit over the stem portion 29 of the connector 28, regardless of the orientation of the flat side portions. The first portion 422 further includes the surface 435 that is sized and shaped to fit beneath the flange 31 of the connector 28 to hold the adaptor 410 against the endoscope 20. The connector 28 extends through the opening 448 and the flange 31 extends over a portion of the surface 435 when the first portion 422 is closely fit onto the accessory channel 30 as shown in FIG. 15. The first portion 422 may also include a closure 430 for closing and securing the second portion 424 as described below. The closure 430 may be connected to the body portion 423 by a pair of flexible legs 426.

The second portion 424 of the adaptor 410 may be connected to the first portion 422 by a hinge 428 as shown in FIGS. 14 and 15. Alternatively, the second portion 424 may be provided separately from the first portion 422 or connected by any means known to one skilled in the art. The adaptor 410 may be provided with the hinge 428 in an open position so that the first portion 422 is laterally slidable over the portion 29 of the connector 28 and beneath the flange 31 and then the second portion 424 may be secured over the connector 28 and to the first portion 422 by the closure 430 connected to a corresponding closure 431 on the second portion 424. The flange 31 is secured between the first portion 422 and the second portion 424 of the adaptor 410. In some embodiments, the closure 430 is formed integrally with the first portion 422 and snaps over the closure 431 of the second portion 424 to secure the adaptor 410 to the connector 28 of the accessory channel 30. Alternatively, the closure 430 may be provided as a separate piece that secures the first portion 422 together with the second portion 424 and onto the connector 28. The second portion 424 may also include gripping members 440 to facilitate closure of the second portion onto the first portion.

As shown in FIG. 14, the second portion 424 may include a recess 432 that is sized and shaped to receive the connector 28 and form a seal against the connector 28. Similar to the embodiment described above, a separate sealing member 434 may be provided to allow the elongate medical device to pass through the sealing member 434 and prohibit fluid and contamination from entering or exiting the adaptor 410. The second portion 224 includes an opening 444 defined through the second portion 424 having the seal 434 therein and operably connecting to the opening 40 of the accessory channel 30 of the endoscope 20. A luer-type connector 450 may be provided at the opening 444 for simple connection of an elongate medical device to the adaptor 410. Any type of connector 450 that connects with the desired elongate medical device may be provided on the second portion 424 of the adaptor 410. The elongate medical device can be connected to the connector 450 of the adaptor 410 so that the shaft of the elongate medical device extends through the openings 444 and 40 and into the accessory channel 30. FIG. 16 illustrates the adaptor 410 secured to the portion 29 of the accessory channel 30 and the second portion 424 secured to the first portion 422 and the flange 31 therebetween. An elongate medical device may be connected to the connector 450 and the device inserted through the opening 444. The seal may be provided so that the elongate medical device may be inserted through the seal and liquids do not escape.

Figure 17:
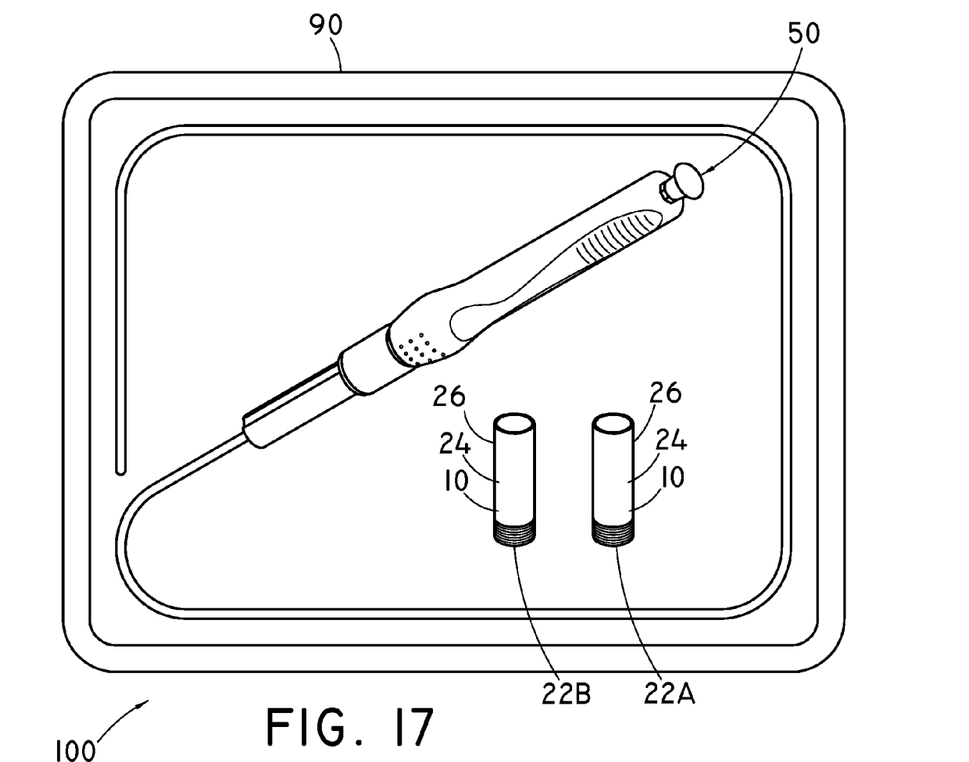
FIG. 17 is a top view of a kit including the adaptor of the present invention and an elongate medical device.
Figure 18:
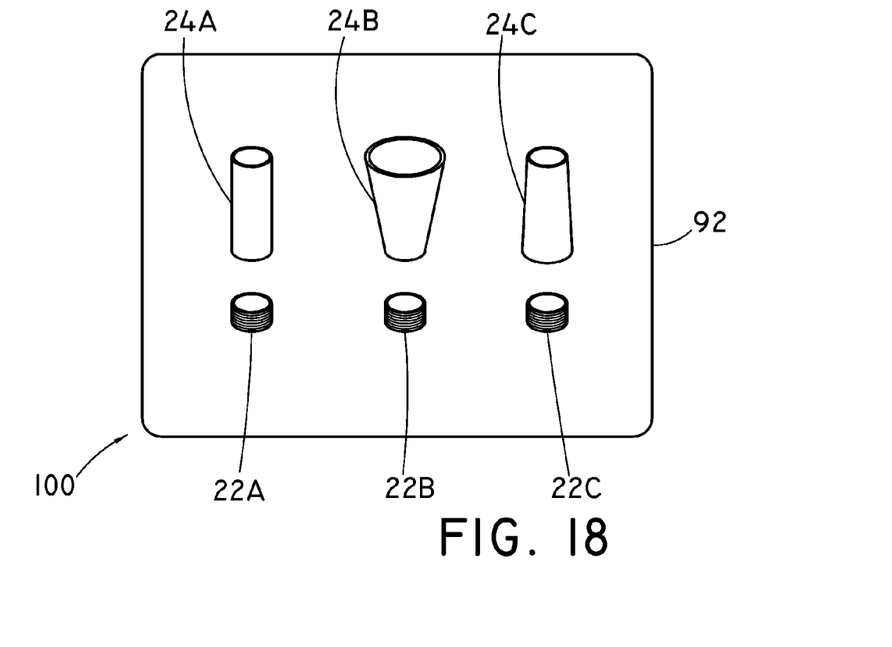
FIG. 18 is a top view of a kit including a plurality of adaptors.

The adaptors described herein may also be provided in a kit 100. The kit 100 may be provided with sterile or non-sterile components. As shown in FIG. 17, at least one adaptor 10 may be provided together with the elongate medical device 50 in the kit 100 having a packaging 90. In some embodiments, the kit 100 may include a plurality of adaptors 10 with or without an elongate medical device 50. The plurality of adaptors 10 of the kit 100 may include a single first portion 22 and a plurality of differently shaped second portions 24. Alternatively, the plurality of adaptors 10 of the kit 100 may include a plurality of differently shaped first portions 22 with a single second portion 24. In some embodiments, the kit 100 may include a plurality of adaptors 10 having a plurality of first portions 2 and a plurality of second portions 24. When the plurality of adaptors are provided in the kit 100 with an elongate medical device, each adaptor 10 includes the second portion 24 having a proximal end portion 26 configured to complimentarily engage the medical device 50 provided in the kit 100. Each adaptor 10 may be provided with differently configured first portions 22a, 22b that can mate with different types of endoscopes. For example, the first end portion 22a may be configured to complimentarily engage the connector of the endoscope where the connector includes a pair of flat sides. The first end portion 22b may be configured to complimentarily engage the connector of the endoscope having a rounded base with a flange, for example, a typical luer connector. The kit 100 may contain 1, 2, 3 or more differently configured first ends 22 of the adaptor 10 so the medical device 50 may be used with any endoscope the physician prefers. The kit 100 may also be provided without the medical device and include a plurality of adaptors 10. The adaptors 10 may include differently configured first portions 22 and second portions 24. As shown in FIG. 18, the kit 100 includes a packaging 92 and a plurality of first portions 22a, 22b, 22c and a plurality of second portions 24a, 24b, 24c that may be provided in a sterile kit. The kit may also be non-sterile. The first portions 22a, 22b, 22c and the second portions 24a, 24b, 24c may be interchangeable so that any first portion engages any second portion to provide a universal adaptor 10. Alternatively, a plurality of differently configured adaptors having first and second portions that are already connected or integrally connected may be provided.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims. For example, the invention has been described using a medical device having a slidable handle and shaft for illustrative purposes only. Application of the principles of the invention to any other elongate medical device are within the ordinary skill in the art and are intended to be encompassed within the scope of the attached claims.

The invention claimed is:

1. An adaptor for connecting an elongate medical device to an endoscope, the elongate medical device and the endoscope having non-compatible connectors, the adaptor comprising:
a first portion having a distal end sized and shaped to connect to an endoscope, the first portion having a first opening defined therethrough; and
a second portion connectable to the first portion and including a second opening defined through the second portion and operably connectable to the first opening, the second portion having a connector comprising a luer-type connector at a proximal end portion of the second portion, the luer-type connector extending proximally from the proximal end portion, the connector sized and shaped to receive at least a portion of the elongate medical device so that a shaft of the elongate medical device is extendable distally through the first opening and the second opening and into the endoscope when the elongate medical device is connected to the adaptor.

2. The adaptor of claim 1 wherein the first portion and the second portion are separate, connectable portions.

3. An adaptor for connecting an elongate medical device to an endoscope, the elongate medical device and the endoscope having non-compatible connectors, the adaptor comprising:
a first portion having a body shaped to connect to an endoscope, the first portion having a first opening defined therethrough; the first portion laterally engagable with the connector on the endoscope such that a surface of the first portion abuts a portion of a flange of the connector; and
a second portion connectable to the first portion and including a second opening defined through the second portion and operably connectable to the first opening, the second portion having an adaptor connector at a proximal end portion, the adaptor connector sized and shaped to receive at least a portion of the elongate medical device so that a shaft of the elongate medical device is extendable distally through the first opening and the second opening and into the endoscope when the elongate medical device is connected to the adaptor.

4. The adaptor of claim 1, wherein the first portion and the second portion are hingedly connected.

5. The adaptor of claim 1, further comprising a seal positionable between the second portion and the endoscope.

6. The adaptor of claim 1, wherein the first portion comprises a closure member to secure the first portion to the second portion.

7. The adaptor of claim 1, wherein the second portion further comprises a recess that is sized and shaped to receive a flange of a connector of the endoscope.

8. The adaptor of claim 3, wherein the first portion comprises a threaded surface and the second portion comprises a threaded surface that mates with the first potion threaded surface to secure the first and second portions together.

9. The adaptor of claim 3, wherein the second portion comprises a securing portion configured to secure the elongate medical device to the adaptor.

10. The adaptor of claim 9, wherein the securing portion is configured to engage a securing portion on the elongate medical device.

11. The adaptor of claim 9, wherein the securing portion comprises a thumb screw.

12. The adaptor of claim 3, wherein the second portion includes one of a key or a keyway configured to mate with the other of the key or the keyway on the elongate medical device to rotationally orient the medical device.

13. The adaptor of claim 3, further comprising a seal positionable between the second portion and the endoscope.

14. The adaptor of claim 3, further comprising a snap-fit closure member connecting the first portion and the second portion so that the first portion and the second portion contact the connector and secure the adaptor to the endoscope.

15. The adaptor of claim 3, wherein the opening is defined through a side of the body and the opening sized and shaped to laterally engage the endoscope.

16. The adaptor of claim 3, further comprising arms extending between the body and a closure member, the arms spaced apart for lateral reception of the endoscope connector therethough.

17. The adaptor of claim 3, wherein the second portion further comprises a recess that is sized and shaped to receive a flange of a connector of the endoscope.

18. The adaptor of claim 3, wherein the adaptor connector of the second portion comprises a luer-type connector.

19. A kit for connecting an elongate medical device to an endoscope, the kit comprising:
an adaptor comprising:

a first portion having a distal end sized and shaped to connect to an endoscope, the first portion having a first opening defined therethrough, the first portion laterally engagable with the connector on the endoscope;

and a second portion connectable to the first portion and including a second opening defined through the second portion and operably connectable to the first opening, the second portion having a connector at a proximal end portion sized and shaped to receive at least a portion of the elongate medical device so that a shaft of the elongate medical device is extendable distally through the first opening and the second opening and into the endoscope when the elongate medical device is connected to the adaptor; and packaging to enclose the adaptor.

20. The kit of claim 19, further comprising an elongate medical device provided in the packaging.

* * * * *